US012711753B2

(12) United States Patent
Mao et al.

(10) Patent No.: US 12,711,753 B2
(45) **Date of Patent: *Aug. 18, 2026**

(54) AUTOMATICALLY IDENTIFYING REGIONS OF INTEREST OF AN OBJECT FROM HORIZONTAL IMAGES USING A MACHINE LEARNING GUIDED IMAGING SYSTEM

(71) Applicant: Topcon Corporation, Tokyo (JP)

(72) Inventors: Zaixing Mao, Harrison, NJ (US); Zhenguo Wang, Ridgewood, NJ (US); Kinpui Chan, Ridgewood, NJ (US); Jonathan Liu, New York, NY (US); Jongsik Kim, Fort Lee, NJ (US)

(73) Assignee: TOPCON CORPORATION, Tokyo (JP)

( * ) Notice: Subject to any disclaimer, the term of this patent is extended or adjusted under 35 U.S.C. 154(b) by 612 days.

This patent is subject to a terminal disclaimer.

(21) Appl. No.: 17/447,465

(22) Filed: Sep. 13, 2021

(65) Prior Publication Data

US 2021/0407088 A1 Dec. 30, 2021

Related U.S. Application Data

(63) Continuation of application No. 16/212,027, filed on Dec. 6, 2018, now Pat. No. 11,132,797.

(Continued)

(51) Int. Cl.

*G06V 10/82* (2022.01)
*A61B 3/10* (2006.01)

(Continued)

(52) U.S. Cl.

CPC .............. *G06V 10/82* (2022.01); *A61B 3/102* (2013.01); *A61B 3/12* (2013.01); *G06F 18/2413* (2023.01);

(Continued)

(58) Field of Classification Search

CPC ......... G06T 2207/30041; G06T 7/0012; G06T 2207/20081; G06T 2207/20084;

(Continued)

(56) References Cited

U.S. PATENT DOCUMENTS 9,179,834 B2 * 11/2015 Reisman .................. A61B 3/12
10,140,421 B1 11/2018 Bernard et al.

(Continued)

FOREIGN PATENT DOCUMENTS

CN 107423571 A 12/2017

OTHER PUBLICATIONS

Extended Search Report for European Patent Application No. EP 18 24 8134 dated Jun. 6, 2019.

(Continued)

*Primary Examiner* — Golam Sorowar
(74) *Attorney, Agent, or Firm* — McDonald Hopkins LLC

(57) ABSTRACT

A multimodal imaging system and method is capable of taking fundus images, automatically identifying regions of interest (ROIs) of the eye from the fundus images, and performing OCT imaging in the identified ROIs, where the OCT images can provide clinically relevant information for screening purposes. By automatically identifying the ROIs, expert intervention is not required to perform specialized OCT imaging and thus, such imaging and analysis can be provided at more facilities and for more subjects for a lower cost.

15 Claims, 12 Drawing Sheets

Related U.S. Application Data

(60) Provisional application No. 62/611,352, filed on Dec. 28, 2017.

(51) Int. Cl.

| | |
|---|---|
| ***A61B 3/12*** | (2006.01) |
| ***G06F 18/2413*** | (2023.01) |
| ***G06T 7/00*** | (2017.01) |
| ***G06T 7/73*** | (2017.01) |
| ***G06T 12/30*** | (2026.01) |
| ***G06V 10/44*** | (2022.01) |
| ***G06V 10/764*** | (2022.01) |

(52) U.S. Cl.
CPC .......... *G06T 7/0012* (2013.01); *G06T 7/0014* (2013.01); *G06T 7/73* (2017.01); *G06T 12/30* (2026.01); *G06V 10/454* (2022.01); *G06V 10/764* (2022.01); *G06T 2207/10101* (2013.01); *G06T 2207/20081* (2013.01); *G06T 2207/30041* (2013.01); *G06V 2201/03* (2022.01)

(58) Field of Classification Search
CPC ......... G06T 2207/10101; G06T 7/0014; G06T 7/0016; G06T 7/11; G06T 11/00; G06T 11/003; G06T 11/008; G06T 11/60; G06T 2200/24; G06T 2207/10016; G06T 2207/10081; G06T 2207/10088; G06T 2207/10104; G06T 2207/10; A61B 3/12; A61B 3/0025; A61B 3/102; A61B 3/14; A61B 2576/00; A61B 5/7267; A61B 8/5223; A61B 3/00; A61B 3/0058; A61B 3/113; A61B 3/1176; A61B 3/1225; A61B 3/1241; A61B 3/145; A61B 5/002; A61B 5/0022; A61B 5/02007; A61B 5/02028; A61B 5/026; A61B 5/055; G06K 9/4628; G06K 2209/05; G06K 9/0061; G06K 9/00617; G06K 9/6257; G06K 9/6273; G06K 9/00604; G06K 9/4604; G06K 9/6256; G06K 9/6269; G06K 9/628; G06K 2209/051; G06K 9/00; G06K 9/00147; G06K 9/00523; G06K 9/00536; G06K 9/00657; G06K 9/00671; G06K 9/00906; G06K 9/03
See application file for complete search history.

(56) References Cited

U.S. PATENT DOCUMENTS

| | | | |
|---|---|---|---|
| 2009/0309874 A1 | 12/2009 | Salganicoff et al. | |
| 2011/0170751 A1 | 7/2011 | Desai et al. | |
| 2012/0323118 A1 | 12/2012 | Menon Gopalakrishna et al. | |
| 2014/0268046 A1 | 9/2014 | Narasimha-Iyer et al. | |
| 2014/0276025 A1 * | 9/2014 | Durbin ................. | A61B 5/4842 600/407 |
| 2014/0314288 A1 | 10/2014 | Roychowdhury et al. | |
| 2016/0292856 A1 | 10/2016 | Niemeijer et al. | |
| 2018/0089840 A1 * | 3/2018 | Yan ........................ | G16H 30/40 |
| 2018/0144209 A1 | 5/2018 | Kim et al. | |
| 2018/0214087 A1 | 8/2018 | Balaji et al. | |
| 2019/0325215 A1 | 10/2019 | Wang et al. | |

OTHER PUBLICATIONS

Carson Lam et al., "Retinal Lesion Detection with Deep Learning Using Image Patches", Investigative Ophthalmology & Visual Science, vol. 59, No. 1, Jan. 2018, pp. 590-596.

Kaur J, Mittal D., "Segmentation and measurement of exudates in fundus images of the retina for detection of retinal disease", Journal of Biomedical Engineering and Medical Imaging, vol. 2, Issue 1, Feb. 24, 2015, pp. 27-38.

Jayaseelan et al.; "Early Detection of Microaneurysms Using Retinal Fundus Images With Removed Blood Vessel Analysis", International Journal of Pharmaceutical Science and Practice, vol. 4, No. 1, 2015, pp. 1-10.

Tang et al.; "Splat feature classification with application to retinal hemorrhage detection in fundus images", IEEE Transactions on Medical Imaging, vol. 32, No. 2, Feb. 2013, pp. 364-375.

He et al.; "Deep residual learning for image recognition. In Proceedings of the IEEE conference on computer vision and pattern recognition", 2016 (pp. 770-778). arXiv:1512.03385v1 Dec. 10, 2015.

Gulshan V, et al., Development and validation of a deep learning algorithm for detection of diabetic retinopathy in retinal fundus photographs, Jama Original Investigation, Innovations in Health Care Delivery, Nov. 29, 2016. Retrieved from http://jamanetwork.com on Dec. 1, 2016.

Gondal et al., "Weakly-supervised localization of diabetic retinopathy lesions in retinal fundus images", arXiv:1706.09634v1. Jun. 29, 2017.

Bency AJ, Kwon H, Lee H, Karthikeyan S, Manjunath BS., "Weakly Supervised Localization using Deep Feature Maps", European Conference on Computer Vision, Oct. 8, 2016 (pp. 714-731). Springer International Publishing. arXiv:1603.00489v2 Mar. 29, 2016.

Zhou et al., "Learning deep features for discriminative localization", Proceedings of the IEEE Conference on Computer Vision and Pattern Recognition, Dec. 14, 2015. arXiv:1512.04150v1 Dec. 14, 2015.

* cited by examiner

AUTOMATICALLY IDENTIFYING REGIONS OF INTEREST OF AN OBJECT FROM HORIZONTAL IMAGES USING A MACHINE LEARNING GUIDED IMAGING SYSTEM

CROSS REFERENCE TO RELATED APPLICATIONS

This application claims priority to U.S. patent application Ser. No. 16/212,027, filed on Dec. 6, 2018, and entitled "AUTOMATICALLY IDENTIFYING REGIONS OF INTEREST OF AN OBJECT FROM HORIZONTAL IMAGES USING A MACHINE LEARNING GUIDED IMAGING SYSTEM", which claims priority to U.S. Provisional Application Ser. No. 62/611,352, filed on Dec. 28, 2017, and entitled "MACHINE LEARNING GUIDED IMAGING SYSTEM." The contents of these applications are incorporated herein by reference in their entireties.

BACKGROUND

There exist various modalities for imaging the interior of the eye. The information obtained from these modalities can be used to diagnose the state of health of the eye. If combined, the information derived from these modalities can yield important clues as to the diagnosis and prognosis of disease. For example, fundus imaging is a technique that covers a large field of view in one measurement, but only images the outer surface of the eye. Because fundus imaging lacks depth information, fundus imaging by itself does not enable further assessment on abnormalities to the interior of the eye. On the other hand, optical coherence tomography (OCT), for example, can provide the depth information. However, the field of view of OCT can be limited and thus can require one to specify a particular scanning region. While 3D OCT exists for larger volumes, the data size is often too large to analyze and manage for vision screening purposes.

Further, due to high costs and technical knowledge often needed to operate OCT systems, OCT systems are typically limited to ophthalmologists who can afford the systems and are trained to identify and manually selected region of interest (ROI) for performing OCT imaging. These ROIs can be identified in advance by knowledgeable specialists (such as ophthalmologists) based on an en-face ophthalmoscopy image (e.g., from fundus imaging). For example, fundus imaging may be first used to identify retinal lesions (or other abnormalities) visible on the outer surface of the eye. Regions including these lesions could then be identified as ROIs by the specialist, so that the ROIs can then be subjected to further imaging via OCT.

While OCT systems have become more affordable and available for use together with traditional a fundus cameras, many users are still not experienced enough to take full advantage of the capabilities of both imaging modalities. In particular, it is challenging to find an appropriate ROI for the OCT imaging based on an en-face fundus image. This difficulty is exacerbated if imaging is done for screening purposes, where time is limited and the type of disease, if any, is unknown. Due to this, selecting an appropriate ROI is subject to human error and is constrained by the user's knowledge. Even to the extent ROI selection has been automated, the automation is still based on a set of manually defined rules (e.g., colors, orientations, area size), which may only be based on or useful for identifying a particular known disease. Because the manually defined rules are unique to each algorithm and each disease, they are limited in their applicability such that many different analyses have to be performed if the disease is unknown.

Consequently, to the extent combined fundus/OCT imaging systems have been proposed, they still suffer from forms of the above deficiencies.

BRIEF SUMMARY

In view of the above, the present disclosure relates to a multimodal imaging system and method is capable of taking fundus images, automatically identifying regions of interest (ROIs) of the eye from the fundus images, and performing imaging in the identified ROIs, where the images can provide clinically relevant information for screening purposes. By automatically identifying the ROIs, expert intervention is not necessarily required to perform specialized imaging and thus, such imaging and analysis can be provided at more facilities and for more subjects for a lower cost.

According to a first example, an imaging method comprises: generating a horizontal image of an object; automatically identifying a region of interest (ROI) of the object based on the horizontal image with a non-fully-supervised machine learning system; and generating a second image of the object within the identified ROI, wherein the second image comprises depth information of the object. In various embodiments of the above example, the horizontal image is a color fundus image; an infrared fundus image; a scanning laser ophthalmoscope (SLO) image; or is derived from 3D optical coherence tomography (OCT) scan data; the second image is an OCT image; the horizontal image is derived from 3D optical coherence tomography (OCT) scan data, and the second image is an OCT image generated by extracting a portion of the 3D OCT scan data corresponding to the identified ROI; the method further comprises discarding portions of the 3D OCT scan data that do not correspond to the identified ROI; the method further comprises displaying the second image; the method further comprise determining probabilities of identified regions of interest, the probabilities indicating a likelihood that the region of interest represents an abnormality of the object as determined by the non-fully-supervised machine learning system; the method further comprises displaying a heat map of the probabilities overlaid on the horizontal image; the second image is generated from a plurality of B-scans of the region of interest; the horizontal image is derived from a 3D survey image and the second image has a greater density than the horizontal image; the horizontal image is a 3D survey image, and the second image is a 3D optical coherence tomography (OCT) image taken of the identified ROI; the method further comprises only storing data corresponding to the second image, or discarding data corresponding to the horizontal image that is not associated with the identified ROI; the object is an eye; the non-fully-supervised machine learning system comprises a convolutional neural network; and/or the ROI is identified by obtaining a class activation map of the non-fully-supervised machine learning system.

According to another example, a method of image analysis with a trained non-fully-supervised machine learning system comprises: receiving a horizontal image of an object from a subject; identifying an abnormality of the object as an output of the trained non-fully-supervised machine learning system based on the received horizontal image; extracting information of the trained non-fully-supervised machine learning used to identify the abnormality; identifying a region of interest within the horizontal image as a region of the horizontal image that contributed to the identification of the abnormality, wherein the non-fully-supervised machine learning system is trained with a plurality of horizontal images of the object from different subjects to identify the abnormality of the object.

According to various embodiments of the second example, the trained non-fully-supervised machine learning system is a convolutional neural network; the abnormality is a retinopathy disorder; the information of the trained non-fully-supervised machine learning system is extracted by determining class activation maps; and/or the region of interest is identified by comparing pixel values of the determined class activation maps to a predetermined threshold.

DETAILED DESCRIPTION OF THE DRAWINGS

Figure 1:
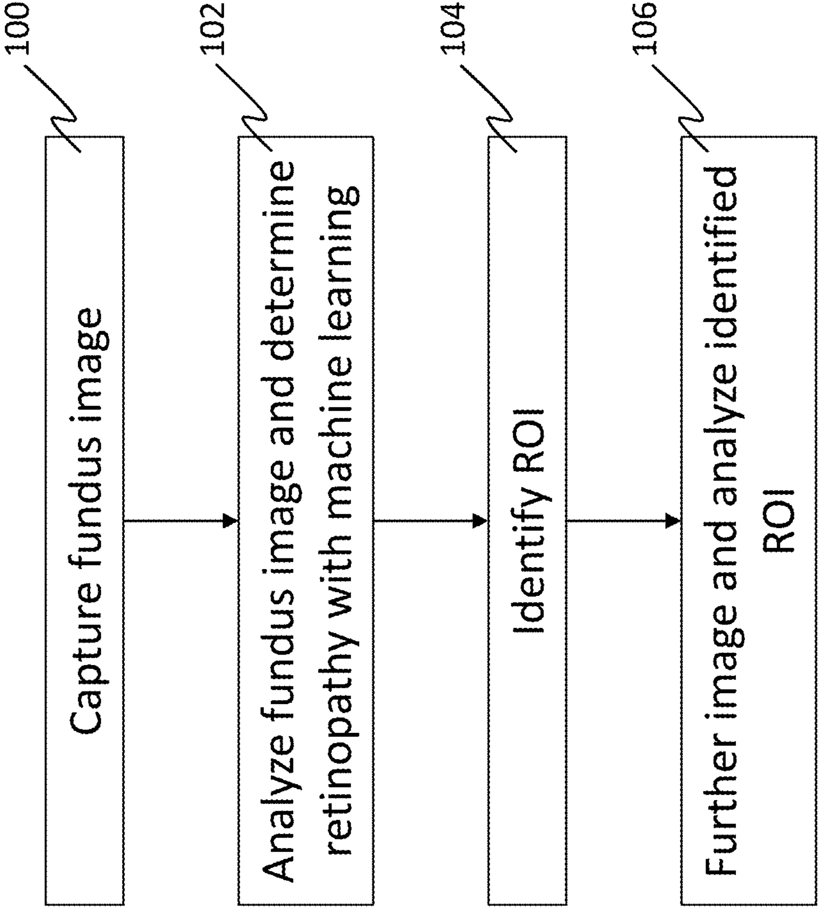
FIG. 1 illustrates an example operation of the systems and methods described herein.

In view of the above, the present description is generally directed to multimodal imaging systems and methods capable of taking fundus images, automatically identifying regions of interest (ROIs) of the eye from the fundus images, and performing OCT imaging in the identified ROIs that can provide clinically relevant information for screening purposes. In so doing, the system and methods described herein may provide automated color fundus plus OCT imaging that does not require expert intervention. Thus, such imaging and analysis can be provided at more facilities and for more subjects. Of course, the description is not limited to fundus and OCT imaging, or even to ophthalmological imaging. Rather, the features described herein could be applied to any complementary imaging modalities, or methods with a common modality, such as MRI, CT, ultrasound, and the like; and to any physiological structures or other objects.

Automatically identifying ROIs comprises automatically detecting retinal abnormalities in the fundus image. The scope of abnormalities that can be detected affects the usability of the resulting imaging system. For example, if the system is only capable of detecting one or a few types of lesions, it would provide little help in identifying an unknown retinopathy (or other disease) of a subject unless that subject's retinopathy happens to be one of the few that the system is capable of detecting. On the other hand, if the system is capable of identifying many types of lesions but takes a long time to analyze (e.g., if one simply combined many specific lesion-specific detection processes), it would provide little help where speed, affordability, and ease of use is desired. In other words, the automatic detection of retinal abnormalities and identification of regions of interest described herein takes into consideration both generality and efficiency of the system.

According to embodiments of the present disclosure, automatic detection of retinal abnormalities and identification of ROIs is performed with machine learning systems. Therewith, a subject's eye is imaged (e.g., by fundus imaging or the like) and the resulting image is input to the machine learning system. The output of the machine learning system provides useful data for further analysis or imaging.

Some machine learning techniques such as deep learning are able to identify that a subject's eye is not healthy, but are not able to identify the particular retinopathy or particular ROIs of the eye/image. This limitation is caused by the fact that, in supervised machine learning, the machine is trained to correctly predict targets (in this case whether the subject is healthy) based on the input (in this case the fundus image of the subject). In order for the machine to predict the location of lesions, one needs to first train it with images labeled at a pixel level. In other words, each pixel in the image is labeled to indicate whether it is part of an imaged lesion. Because this approach is labor intensive and sensitive to the annotator's knowledge, one lesion may be easily missed, which could significantly degrade the sensitivity of the system.

By contrast, weakly supervised (or, non-fully-supervised) machine learning as disclosed hereinafter may help overcome this problem. With weakly supervised learning, instead of outputting the prediction of the target (whether the subject is healthy), information regarding how the prediction is made is extracted from the learnt system. For example, the extracted information can be the location of the lesion or abnormality that the system recognizes and would use to identify a subject as unhealthy. Such a non-fully-supervised machine learning technique can thus, for example, automatically identify a region of interest in an input fundus image, and guide imaging with a second modality (e.g. OCT) in that region of interest. In other words, such weakly supervised machine learning systems may provide general purpose retinal abnormality detection, capable of detecting multiple types of retinopathy. As a result, the systems and methods herein do not depend on the disease type and can be applied to all subjects. This can be particularly helpful for screening purposes.

Briefly, as illustrated in FIG. 1, the systems and methods described operate as follows. First, a fundus or like image is captured 100. The fundus image is then input into a neural network or other machine learning system 102, which analyzes the fundus image and determines, for example, the existence of a particular retinopathy. Using information extracted from the machine learning system (e.g., information relating how the machine determined a particular output based on an input), one or more regions of interest are identified 104. In other words, the present disclosure recognizes that how a machine learning system produces an output (e.g., a retinopathy) based on an input image (e.g., a fundus image of the eye) can be used to identify regions of the image (and correspondingly, the eye) having an abnormality that likely caused the machine learning system to output the particular retinopathy associated with the abnormality. Once identified, those regions can then be more closely studied 106 for example, with additional imaging.

Figure 2:
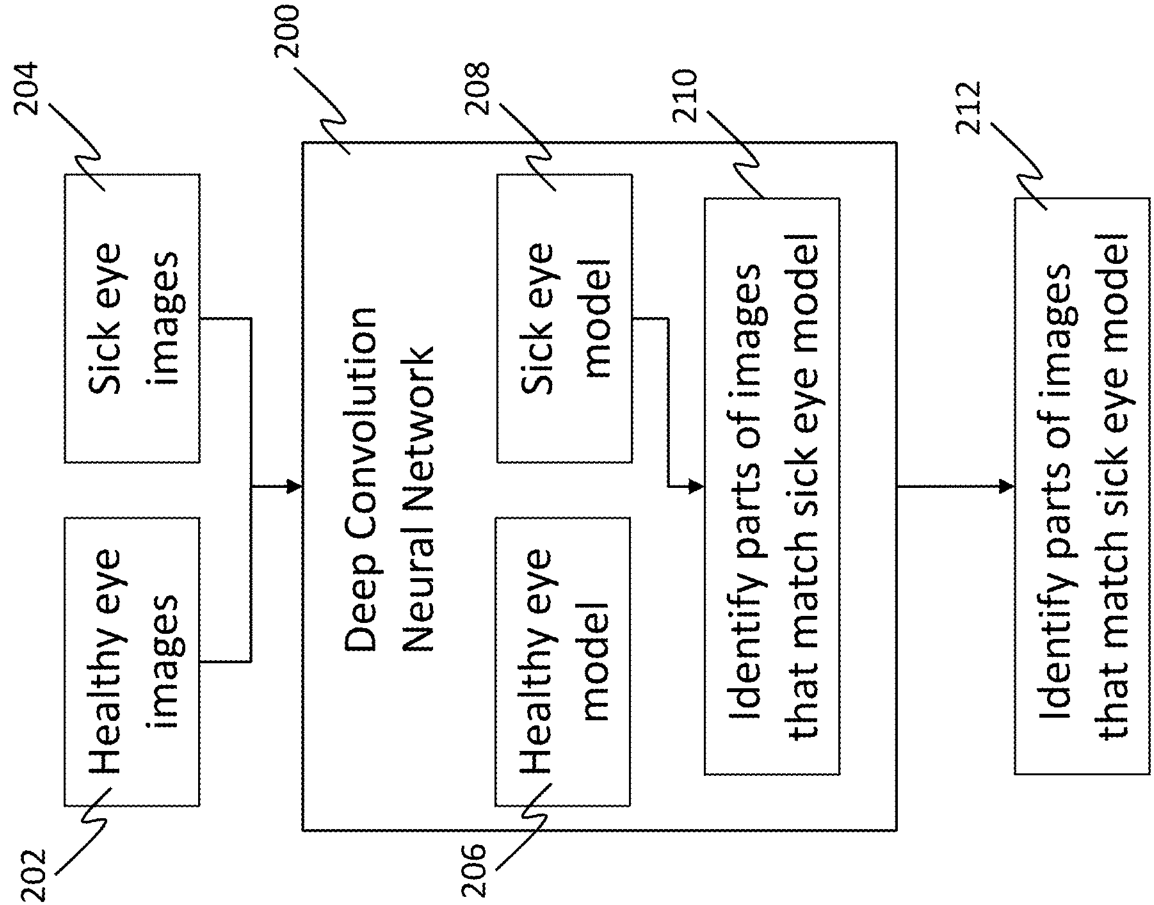
FIG. 2 illustrates an example convolutional neural network framework.

As noted above, the machine learning system may include a neural network. The neural network may be of any type, such as a convolutional neural network (CNN), which is described herein as an example but is not intended to be limiting. The CNN (or other neural network) is trained to distinguish input images (e.g., color fundus images) of healthy and sick eyes. In other words, "under the hood," the CNN constructs models of what fundus images of healthy and sick eyes look like. This framework is illustrated by the flowchart in FIG. 2. As seen therein, a deep convolution neural network 200 is trained by inputting known images of healthy eyes 202 and sick eyes 204. Based on these known images 202, 204, the neural network 200 is able to construct a model 206 what a healthy eye image looks like and a model 208 of what a sick eye image looks like. At a high level, the sick eye model 208 is able to recognize 210 portions of eye images that match known sick eye images. Once trained the neural network 200 is able to output 212 a determination of whether any input image matches the healthy eye model 206 or the sick eye model 208, and what portions of the image match the sick eye model 208. From this, regions where there is an abnormality associated with a retinopathy can be identified; for example, as the regions where an input fundus image matches the sick eye model 208.

Figure 3:
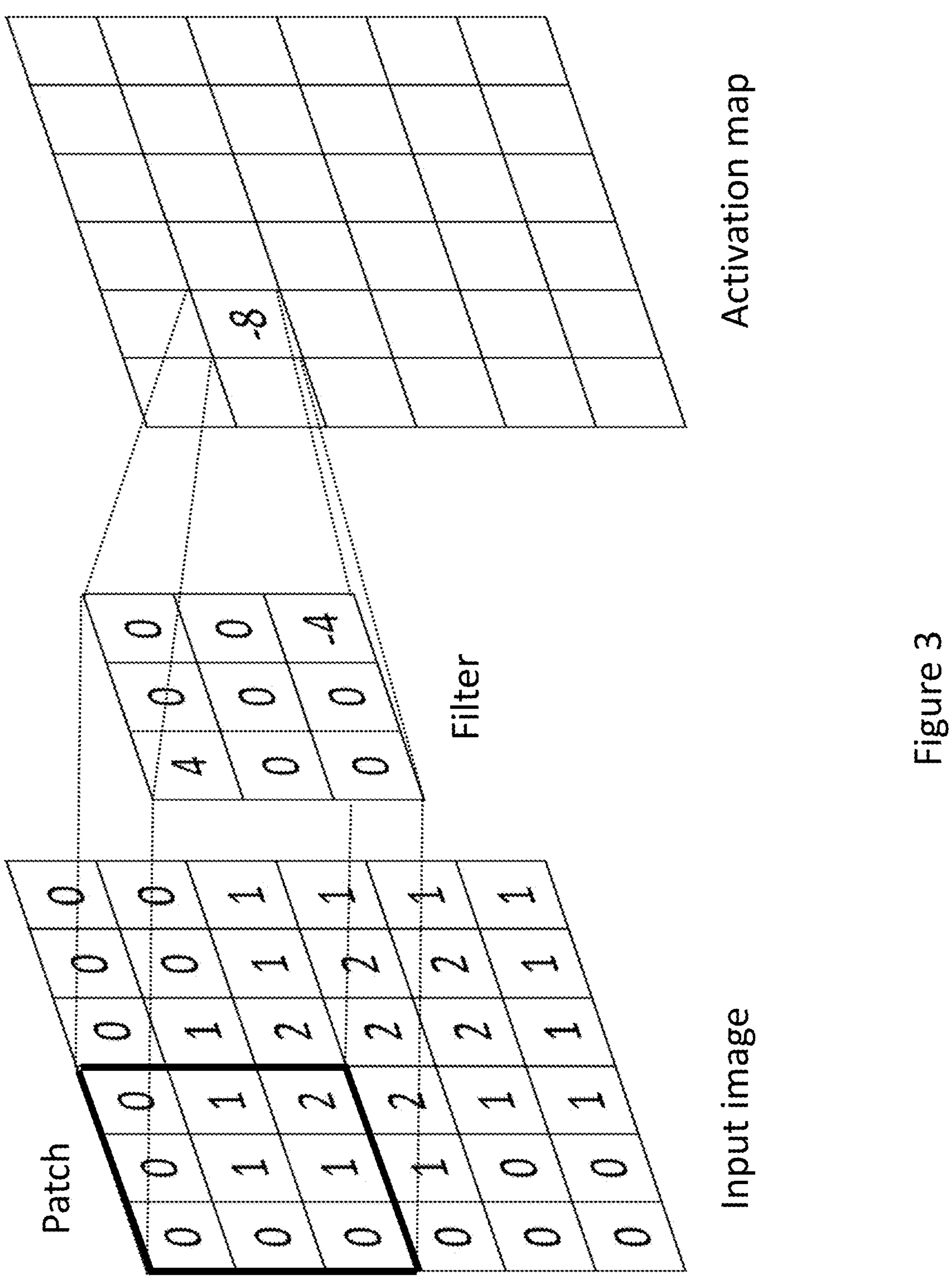
FIG. 3 illustrates an example convolution layer of a convolutional neural network.

CNNs are a type of machine learning modeled after the physiological vison system of humans. As illustrated in FIG. 3, the core of a CNN comprises convolution layers including a filter and an activation map. As shown therein, the filter (also known as a kernel) looks at a small patch of an input image (having 6×6 pixels in the example of FIG. 3) at a time, and calculates an activation value for a corresponding pixel in the activation map. The patch (having 3×3 pixels) is the same size as the filter. Applying the filter to the entire input image generates the activation values for each pixel of the activation map. The activation value is determined by performing a convolution operation on the pixel values of the patch of the input image and the filter. Thus, the closer the pattern of a small patch of the input image matches the pattern of the filter, the higher the activation value; conversely the less they match, the lower the activation value. Of course, this relationship could be reversed based on the operation, so long as the meaning of the resultant value is understood. In this way, the filter effectively "filters" the input image to an activation map based on its content. The particular combination of filters and convolution layers constitute the particular machine learning model.

According to the example of FIG. 3, the convolution operation sums the product of the value of each filter pixel value and the value of the corresponding input image pixel and assigns the summation value as the activation value for a pixel of the activation map corresponding to the middle pixel of the filter. In other words, the operation corresponds to a pixel-wise multiplication between the patch and the filter. Thus, the activation value for the pixel in the second row and second column of the activation map (performed on a patch including the first three rows and columns of the input image identified by the bold outline) in the example of FIG. 3 is equal 0×4+0×0+0×0+0×0+1×0+1×0+0×0+1×0+2×(−4)=−8.

While the shape of a filter may seem limited and constrained by its size, the CNN may stack multiple convolution layers in series, effectively applying multiple filters, each with a different purpose/function to the input image. Thus the filters of the CNN can be designed to be capable of identifying complex objects.

As noted above, the CNN can be trained by inputting images (e.g., fundus images) and a known retinopathy (e.g., healthy or sick, including an identification of a particular disease) associated with each image. During training, the CNN learns the set of filters that best separates images of healthy and sick subjects and estimates a probability that the subject is sick/has a particular retinopathy. Thus, information of retinal abnormalities can be found in the learnt filters of a trained CNN for a particular retinopathy. In other words, learnt filters contain the information that can be used to identify potential regions of interests (e.g., by identifying locations where lesions appear in the fundus image). When this information is extracted from the learnt filters, it can then be applied back to the input image to identify those regions of interest by identifying which portions of the input image match the sick models.

To this end, class activation maps (CAMs) or like methods can be used to retrieve the information in the learnt filters of a CNN. The descriptions herein related to CAMs are merely examples, and the present disclosure is not limited to CAMs; rather, any method for extracting information of a learnt neural network or other machine learning algorithm may be used. In this example, a CAM is retrieved by attaching a global activation pooling (GAP) layer to the final convolution layer of the CNN. The GAP reduces the final activation maps having many pixels into a single (or at least fewer) representative value(s). For example, assuming the final convolution layer has k filters and the activation map of the k-th filter is $A_k$, the GAP is determined as the average value of all the pixels (where i,j indicates the i-th and j-th pixel) in the activation map $A_k$ of the k-th filter according to:

$$G^k = \frac{1}{\text{number of pixels}} \sum_i \sum_j A^k_{i,j} \quad \text{(Equation 1)}$$

Figure 4:
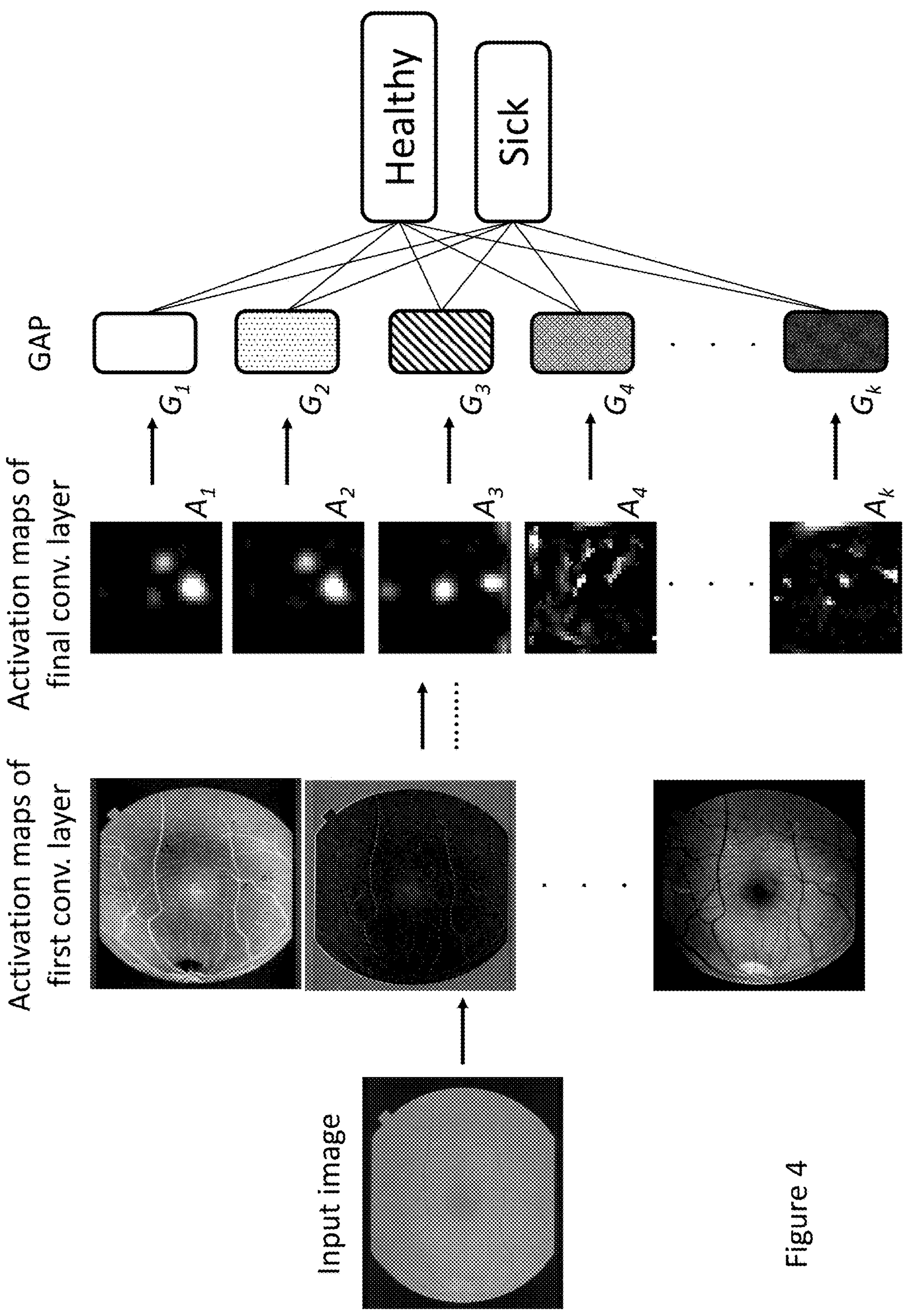
FIG. 4 illustrates an example of a convolutional neural network with multiple convolution layers and an attached global activation pooling layer.

FIG. 4 illustrates an example of a CNN with multiple convolution layers and an attached GAP layer. As seen therein, a fundus image is input to the CNN, which at a first convolutional layer applies a plurality of filters to generate a corresponding plurality of activation maps (three shown). Each of these activation maps is then applied as an input to additional convolution layers. At the final convolution layer, a plurality of filters is again applied to generate a corresponding plurality of activation maps (five shown, identified as $A_1$-$A_4$ and $A_k$) that are used to determine a corresponding plurality of GAPs (for example, according to Equation 1). Collectively, the GAPs are used to determine probabilities of whether the input image is of a healthy or a sick eye.

According to one example, the probability that the input image is of a sick subject is calculated according to:

$$z_{healthy} = \sum_k w^k_{healthy} \cdot G^k \quad \text{(Equation 2)}$$

$$z_{sick} = \sum_k w^k_{sick} \cdot G^k \quad \text{(Equation 3)}$$

$$p(\text{sick}) = \frac{\exp(z_{sick})}{\exp(z_{healthy}) + \exp(z_{sick})} \quad \text{(Equation 4)}$$

where $$w^k_{healthy}$$

and $$w^k_{sick}$$

are weights connecting the classification and the different GAPs $G_k$. For example, if $G_k$ indicates the presence of drusen, $$w^k_{healthy}$$

could be negative and $$w^k_{sick}$$

could be positive. The weights may be randomly initialized and adjusted during training of the machine learning system such that $z_{healthy}$ is higher for healthy training images and $z_{sick}$ is higher for diseased training images.

Finally, the CAM can be calculated according to:

$$C_{i,j} = \sum_k w^k_{sick} \cdot A^k_{i,j} \quad \text{(Equation 5)}$$

where $C_{i,j}$ indicates the likelihood that a pixel (i, j) is part of a lesion. In some embodiments, $C_{i,j}$ can further be rescaled to be $\in [0,1]$. By setting a threshold corresponding to a degree of likelihood that a pixel contains a lesion, individual ROIs can be identified. In other words, an ROI of the eye corresponding to a particular pixel of an input image could be identified where $C_{i,j}$ for that pixel is greater than the threshold.

Figure 5:
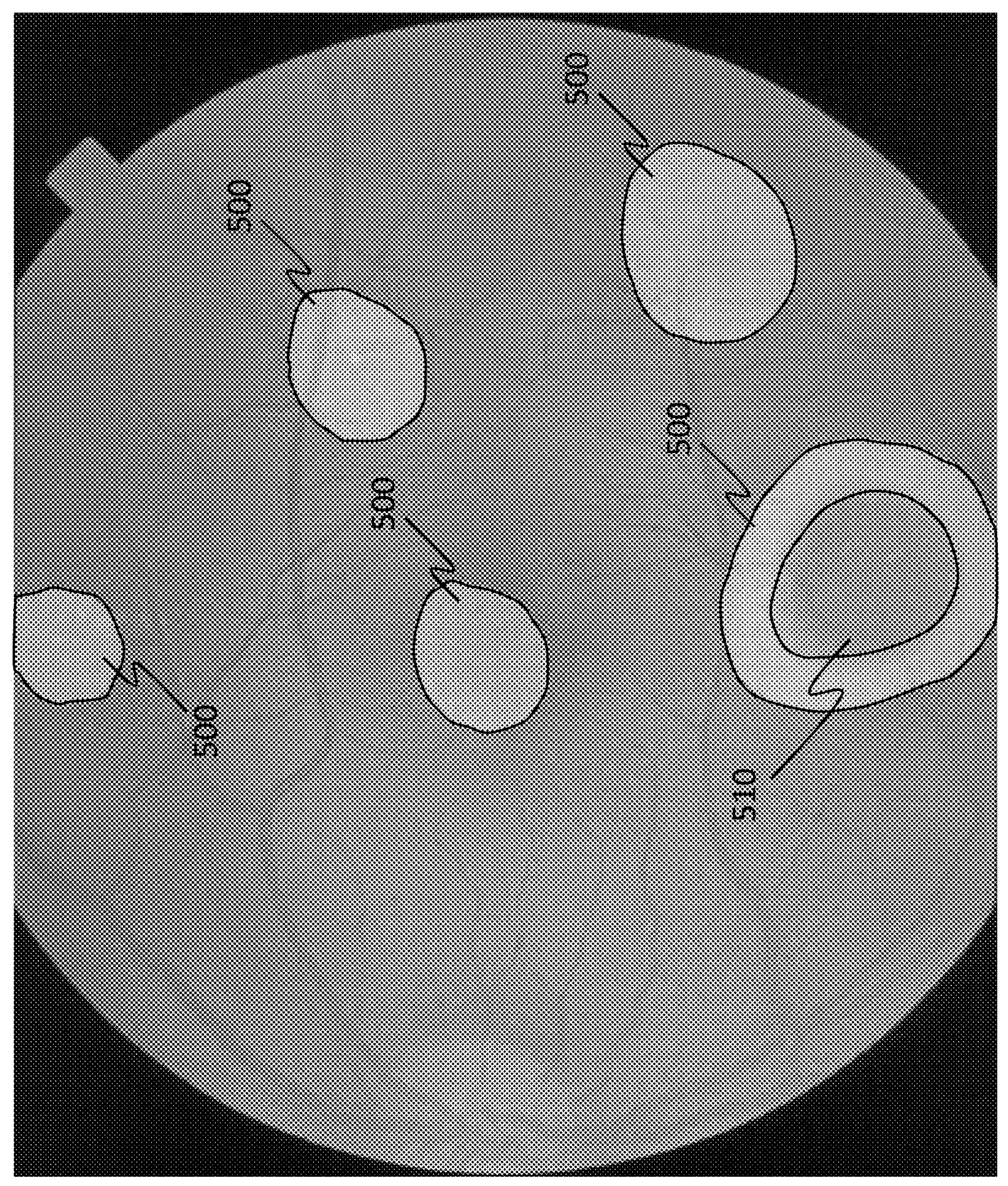
FIG. 5 is an example heat map indicating the detected abnormality regions and probabilities of an abnormality.

For example, FIG. 5 is a heat map indicating detected abnormality regions and probabilities of an abnormality of the CAM as superimposed on an input fundus image. The heat maps herein are images of the eye (e.g., the horizontal, surface, or en face images) having a color, shade, hue, or the like corresponding to a probability that the region includes an abnormality. This produces a resultant image of the eye whereby the probability of an abnormality in any particular portion of the eye is represented as a color, shade, hue, or the like in the image. Regions 500 each represent a detected abnormal region, and region 510 (having a darker shade) represents a higher probability of abnormality than regions 500. Of course, the heat maps can be in color such that, for example, color contours highlight the detected abnormal regions and indicate a probability where a color transition from blue to red may indicate an increase in abnormality probability. In the example of FIG. 5, a threshold of 0.4 (where $C_{i,j}>0.4$) was used to identify the regions 500.

Figure 6:
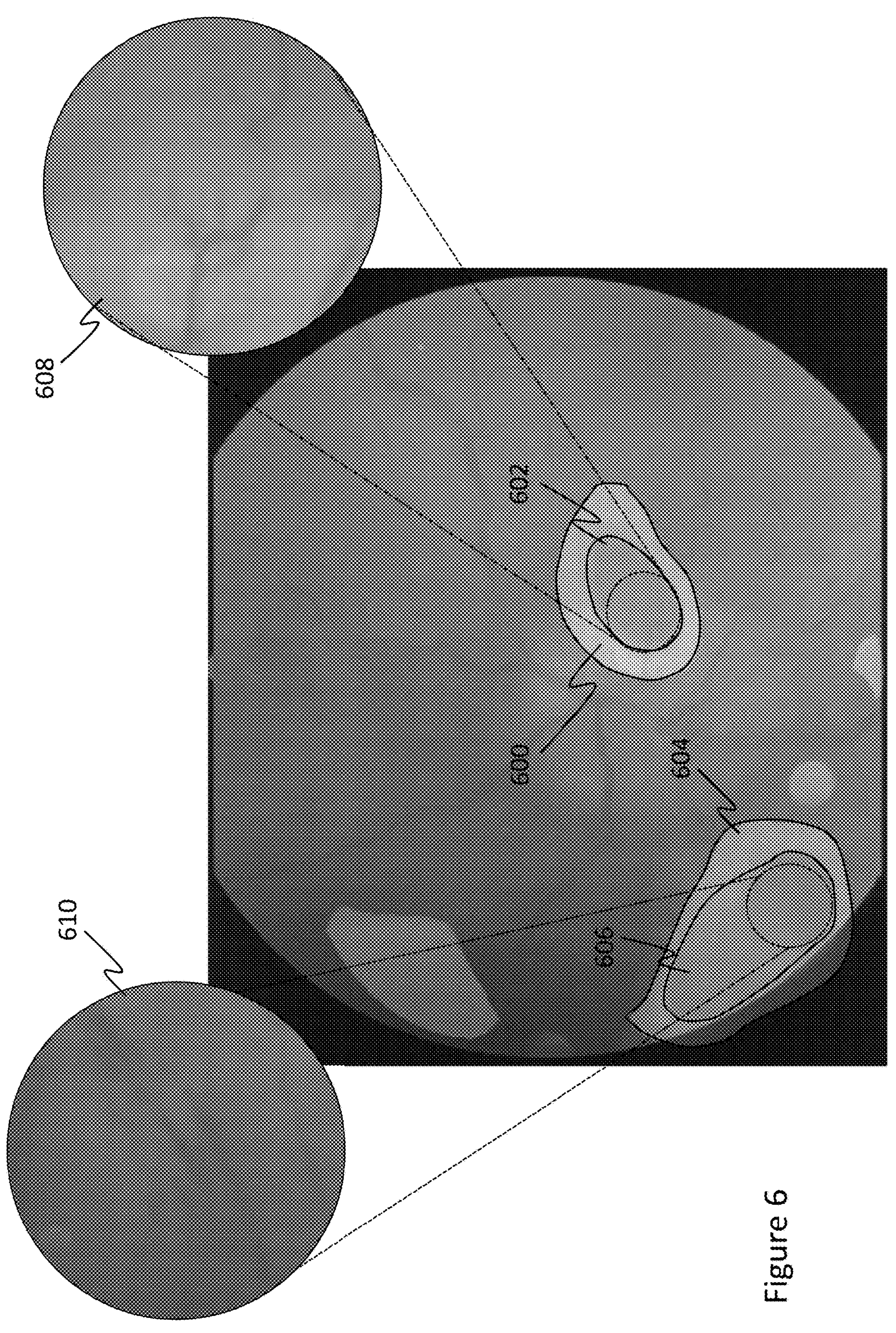
FIG. 6 is an example heat map for an image of an eye having hypertensive and arteriosclerotic retinopathies.
Figure 7:
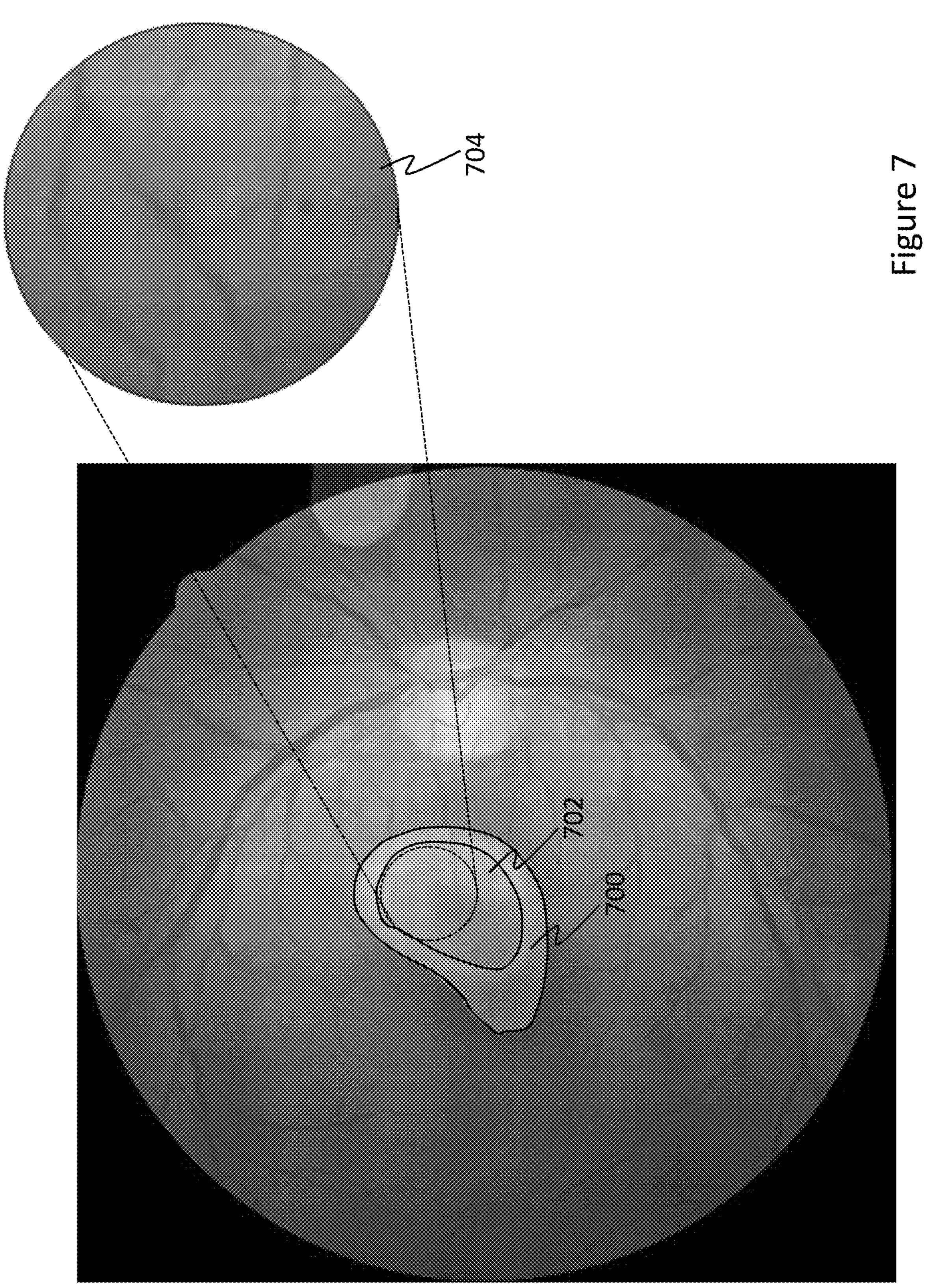
FIG. 7 is an example heat map for an image of an eye having micro-aneurysms.
Figure 8:
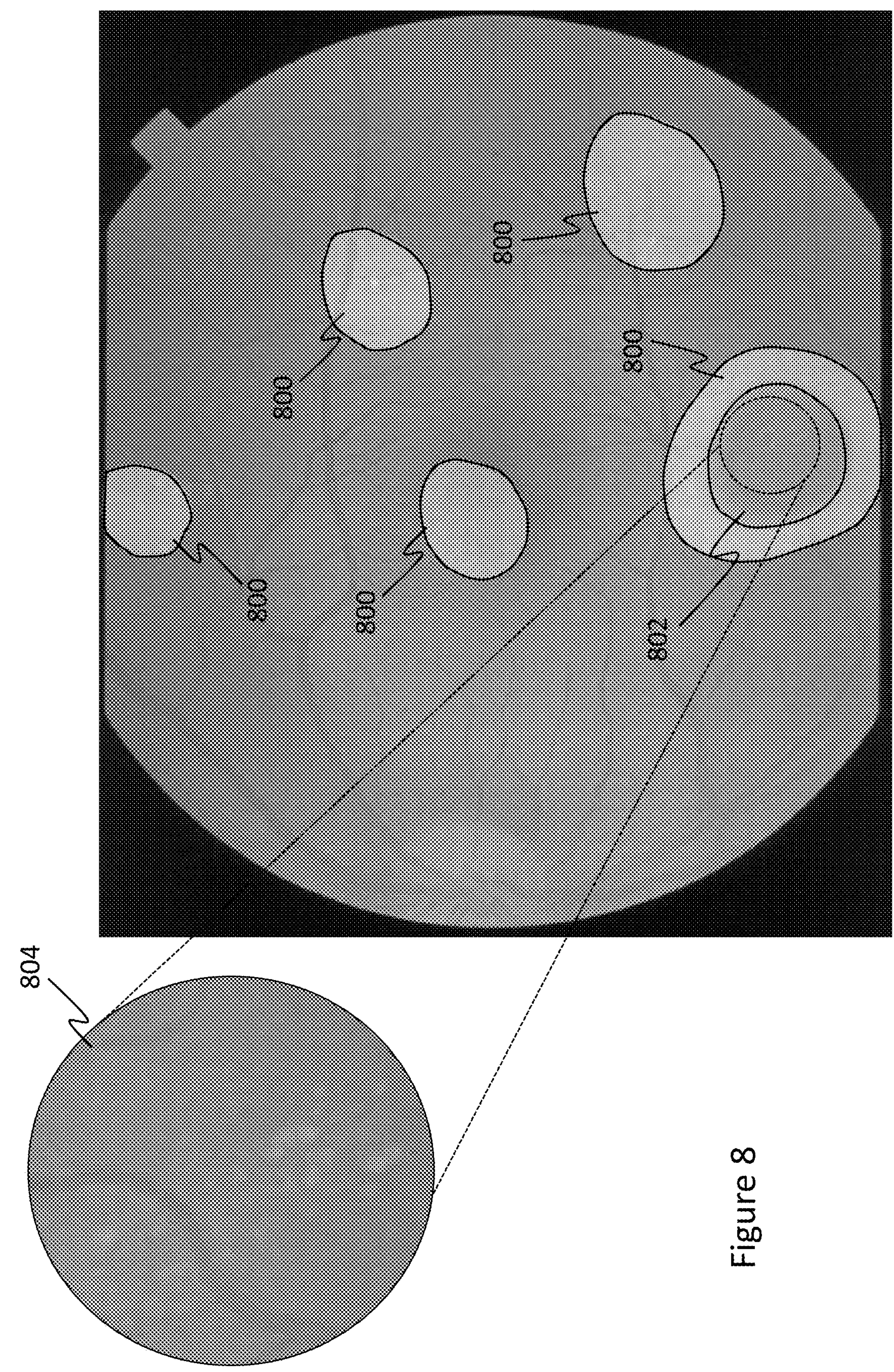
FIG. 8 is an example heat map for an image of an eye having a background diabetic retinopathy.

FIGS. 6-8 further illustrate example CAM heat maps for various retinopathies. Notably, FIG. 6 is a heat map for an image of an eye having hypertensive and arteriosclerotic retinopathies. Therein, the CAM overlay indicates regions 600 and 604 as likely abnormal with regions therein 602 and 606 as having the highest probability of an abnormality. Portions of the image in these high-probability regions 602 and 606 are enlarged, where the structural abnormality can be visually confirmed. Similarly, FIG. 7 is a heat map for an image of an eye having micro-aneurysms. The CAM map indicated region 700 as being abnormal, and therein, region 702 as a having a high probability of being the location of the abnormality. A portion of high-probability region 702 is enlarged 704, which shows visual confirmation of the retinopathy. FIG. 8 is a heat map for an image of an eye having a background diabetic retinopathy. Again, the CAM map indicated regions 800 as likely containing abnormalities, with region 802 having the highest probability of having an abnormality. A portion 804 of high-probability region 802 is enlarged and visually confirms that the abnormality exists.

Using these CAMs and corresponding identified ROIs, a second image can be generated in and/or around the identified ROIs. The second image can be generated by a scan with a second modality (e.g., an OCT scan) that provides more detailed imaging, analysis, and information about the retinopathy. For example, an OCT scan may provide a 3D imaging volume at high resolutions so that the internal structure of retinal tissue may be analyzed, whereas the initial en-face image only images the surface of the structure. In still other examples, the second image can be an OCT-angiography (OCTA) image, visual field test results, fluorescent angiography, or fluorescent angiography fundus image. Examples of the application of CAMs according to the present disclosure are illustrated in FIGS. 9-11.

Figure 9:
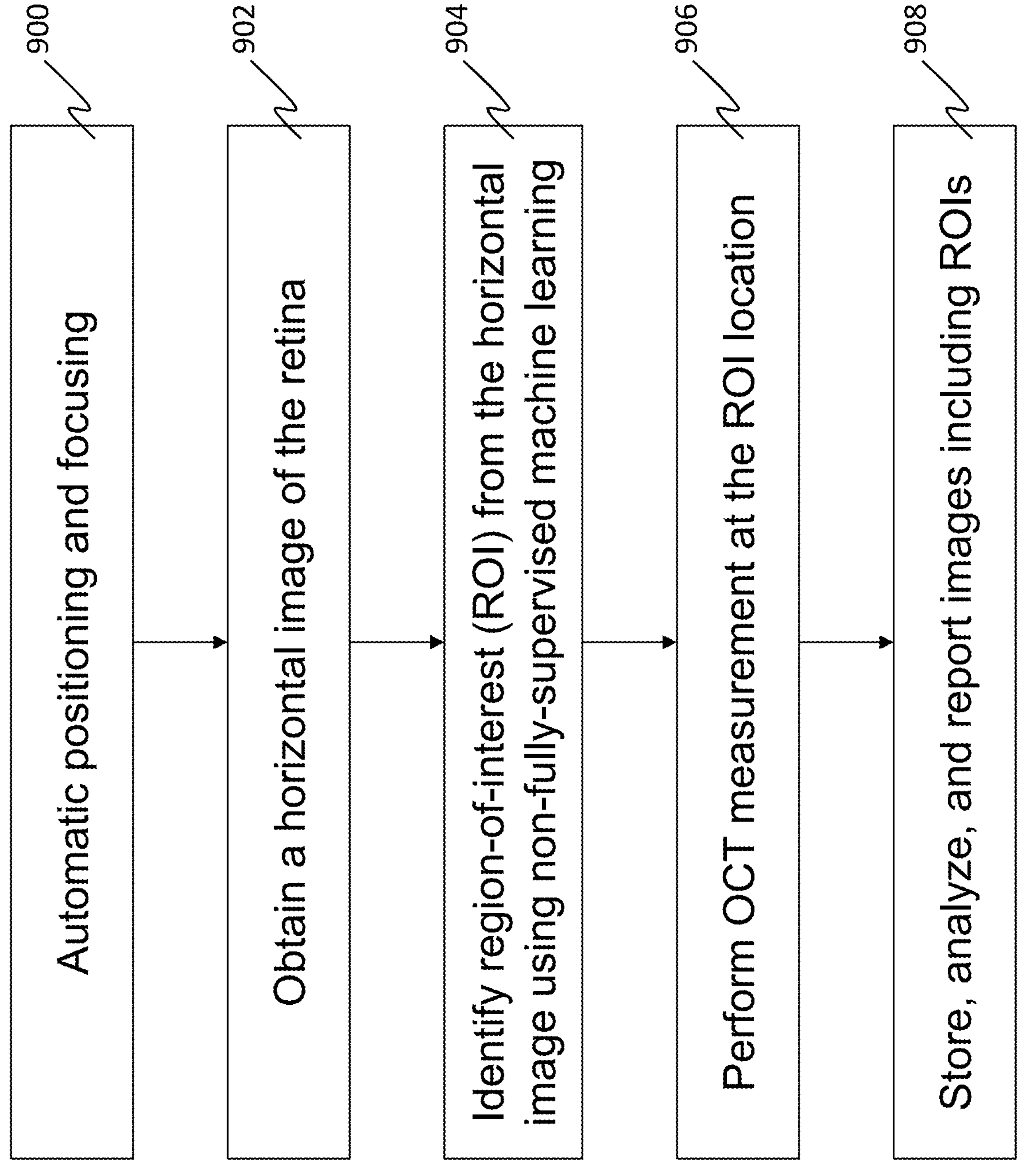
FIG. 9 is a flow chart of an example application of class activation maps.

According to the example application of FIG. 9, a horizontal image of the retina is taken 902 after the imaging modality used to take the image has been automatically positioned and focused 900 on the retina. Herein, a "horizontal" image means a surface or en-face image of the object being imaged, (e.g., the retina). Such an image may be taken with, for example, a fundus camera (color or infrared), scanning laser ophthalmoscope (SLO), or be a surface image derived from a 3D-OCT scan. Of course, other modalities and techniques may be used for horizontal/surface images, and the above examples are not limiting. Then, ROIs are identified from the horizontal images 904 using the above-described non-fully-supervised machine learning and CAMs. Based on these identifications, OCT imaging and measurement is performed 906 on portions of the retina corresponding to the identified ROI locations of the horizontal image. This second imaging of the ROIs may be performed automatically (e.g., OCT imaging may be automatically controlled upon determination of the ROI) or manually instituted by a user. The data from the second image (OCT imaging) and measurements and/or the horizontal imaging is finally reported to a user and stored 908 for future analysis or review. This and other data derived from the method can also be stored, analyzed, and/or reported, for example, in any form of memory, as part of a database or the like (e.g., for future analysis or normative comparisons). The reports may include any of the images, heat maps/CAMs, identification of possible disease/retinopathy, and the like.

Figure 10:
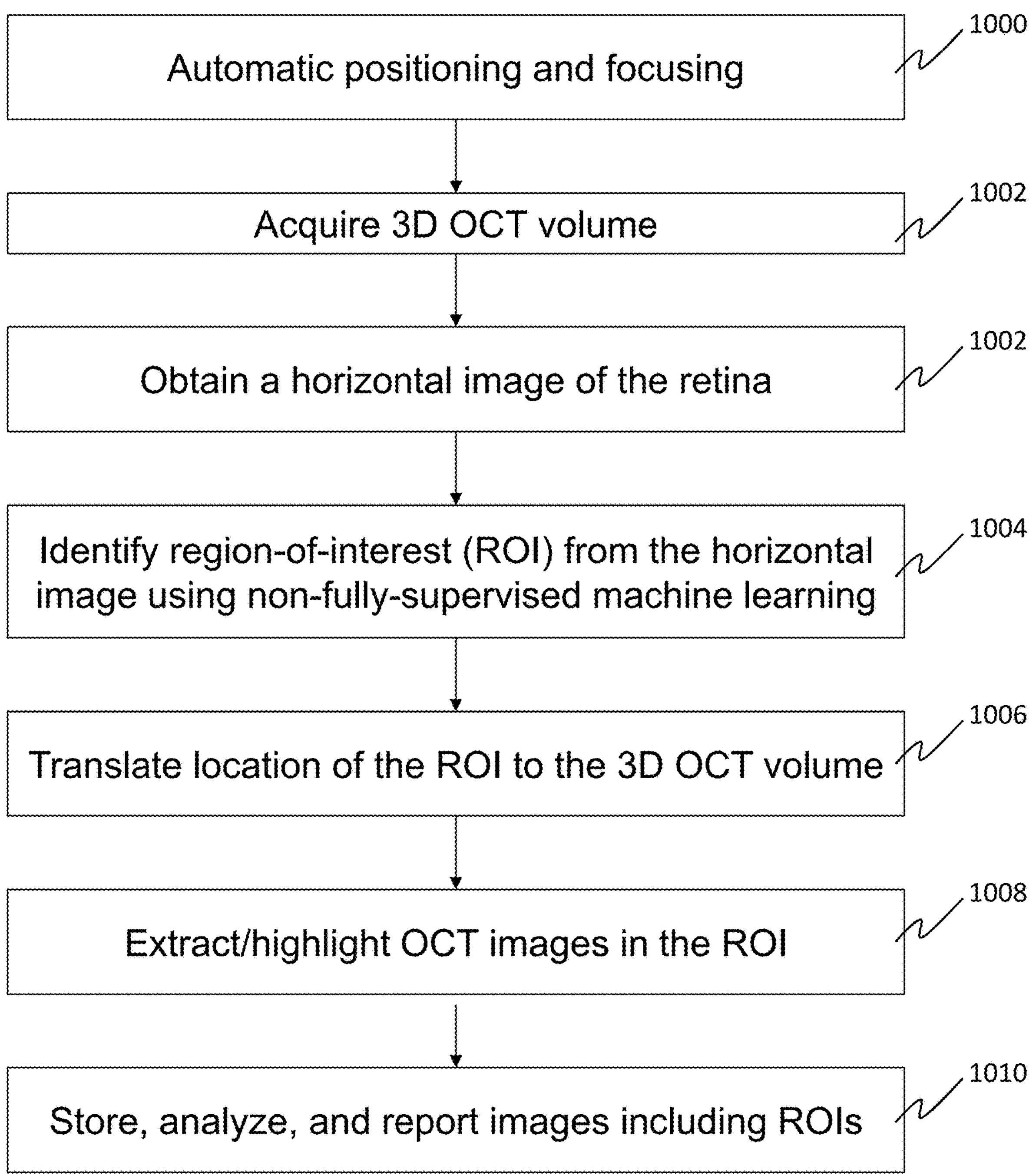
FIG. 10 is a flow chart of another example application of class activation maps.
Figure 11:
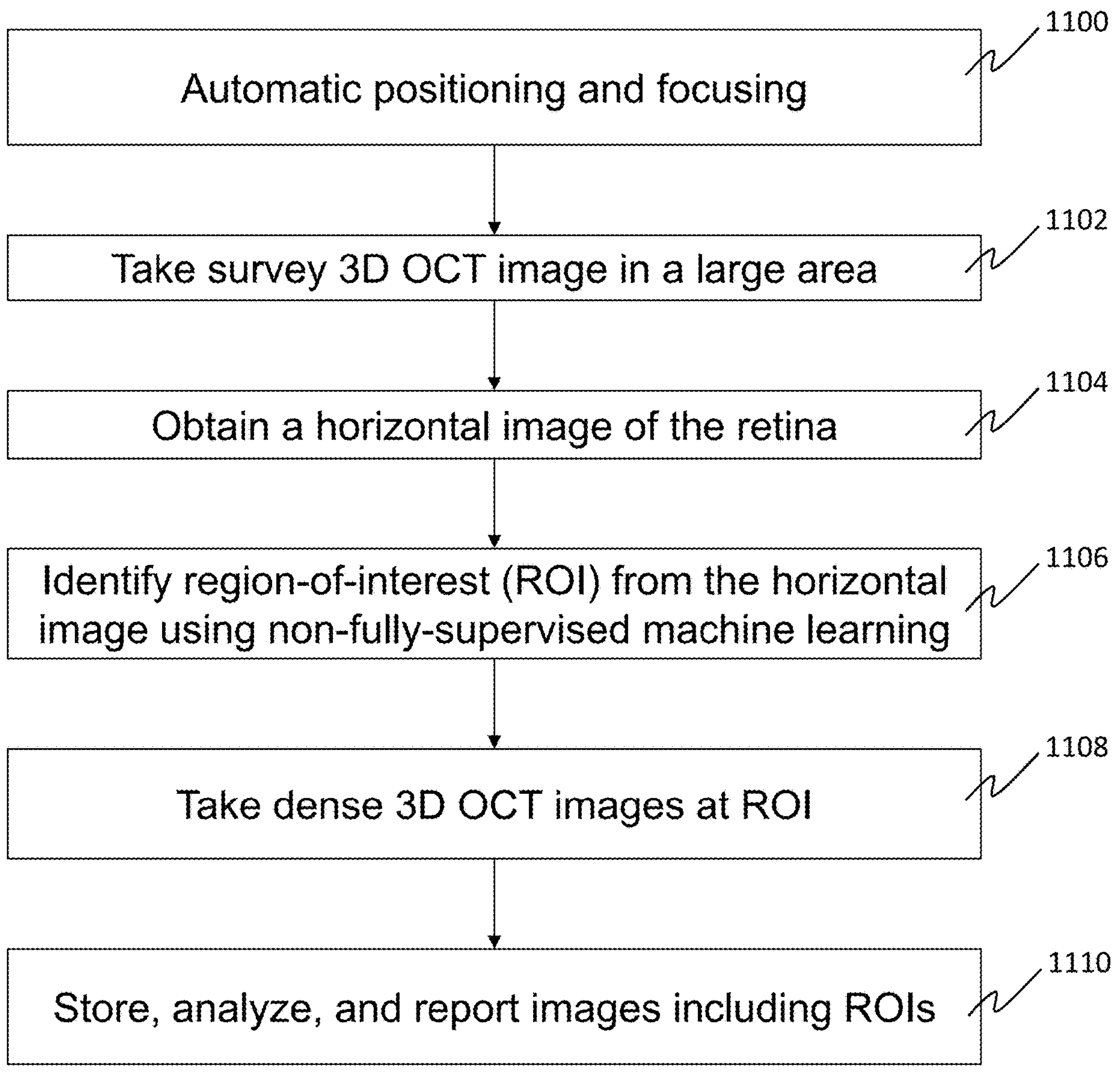
FIG. 11 is a flow chart of another example application of class activation maps.

The application method of FIG. 10 is similar to that of FIG. 9, however, a 3D OCT volume of an eye is initially taken and used to obtain the horizontal image for identifying ROIs. According to this example, a second imaging scan need not be performed because all of the relevant data is captured in the initial 3D OCT volume. More particularly, the OCT imaging modality is initially positioned and focused 1000, and then the 3D OCT volume is acquired 1002. From the 3D OCT volume, a horizontal image is obtained 1004. The horizontal image may be obtained by any technique, for example, flattening the volume along a depth dimension by averaging the pixel values across a relevant depth (Z) at a particular X-Y location of the volume. Again, ROIs are identified 1004 using machine learning and CAMs. The locations of the ROIs are then translated to the original 3D OCT volume 1006 so that the relevant volumetric data corresponding to the ROI can be extracted and/or otherwise highlighted 1008. All of the information including the entire 3D OCT image data can also be stored, analyzed, and/or reported; or, alternatively, the remainder of 3D image data not associated with the ROIs can be otherwise discarded.

The identified ROIs can also be useful 3D OCT scans are performed subsequently to the ROI identification. This is because the horizontal resolution of 3D OCT volumes is inversely proportional to the scan area. Thus, ROIs can guide future OCT scans at higher resolution in the most relevant regions by limiting the scan area to those most relevant regions. In other words, ROIs derived from an initial survey OCT scan that covers a large area, or similar horizontal images from large area scans from a different imaging modality, can be used to generate higher resolution scans in and around the identified ROIs by limiting the scan area. Additionally, instead of overwhelming users with a large 3D volume of data, B-scans can be selected from the ROIs that highlight an anomaly therein.

FIG. 11 illustrates a third application in accordance with the above. The application of FIG. 11 is similar to that of FIG. 8, however, a 3D OCT survey image covering a large area of an eye is initially taken 1102 (after automatic positioning and focusing 1100) and used to obtain the horizontal image of the retina 1104. After identifying ROIs 1106, denser (or higher resolution) 3D OCT images are taken 1108 of the retina at locations corresponding to the ROIs to form the second images. Such denser images can reveal finer and more granular details of the tissue and can better support a particular diagnosis or disease identification, and better aid in analyzing progression of a disease. As above, the dense 3D OCT images, and/or survey image are stored, analyzed, and/or reported 1110.

Figure 12:
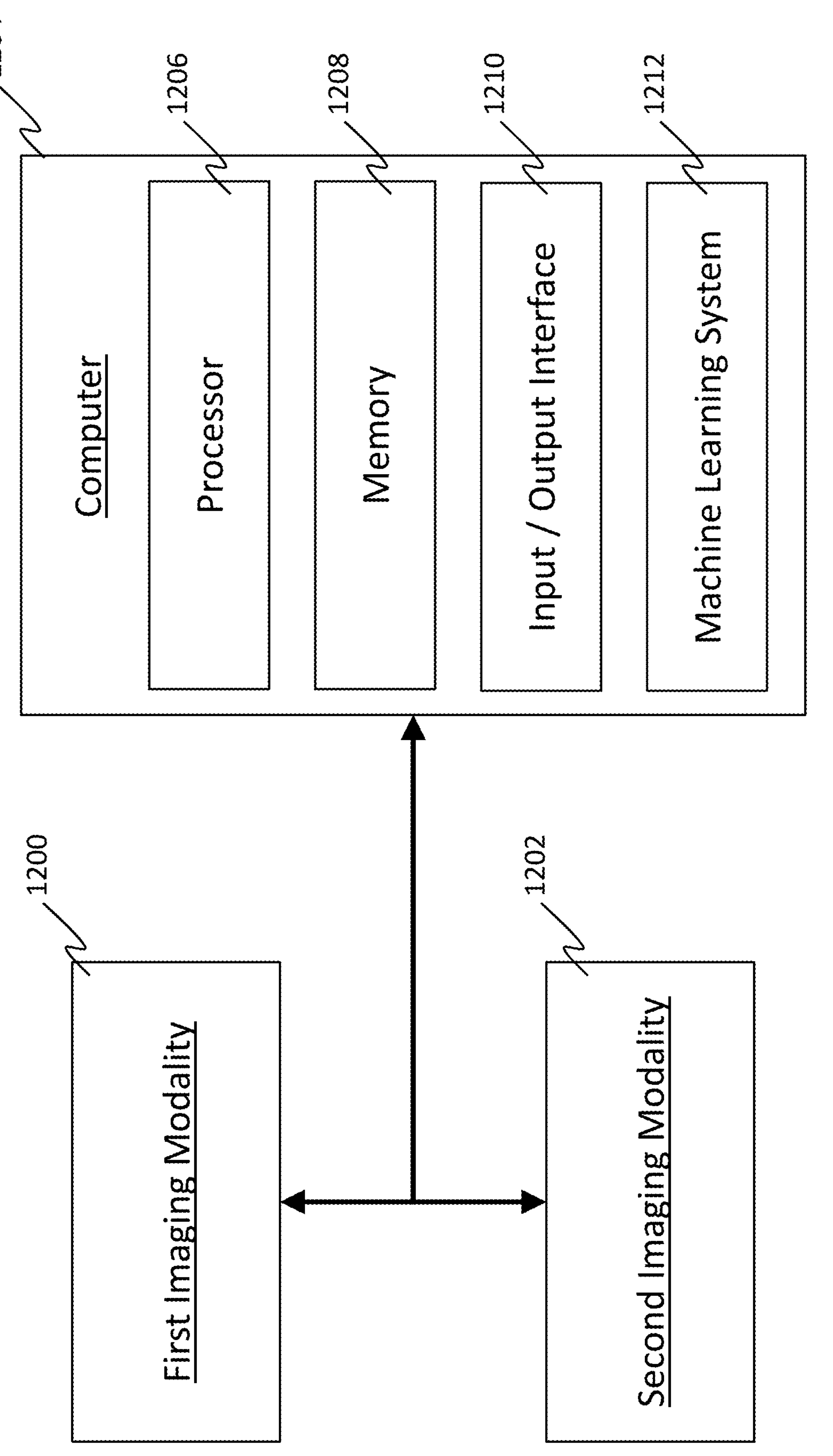
FIG. 12 is a schematic diagram of an example system described herein.

In view of the above, an example system corresponding to the disclosure herein is schematically illustrated in FIG. 12 and comprises a first imaging modality 1200 that is capable of generating a horizontal image, a second imaging modality 1202 capable of generating images of regions of interest identified in the horizontal image, and a computer 1204 having a processor 1206, or the like configured to automatically identify the regions of interest in the horizontal image according to the above method. In view of this, computer further includes at least one processor (e.g., a central processing unit CPU, graphics processing unit GPU, or the like) that is capable of machine learning with, for example, the above-described CNN that forms a machine learning system 1212. The processor of the machine learning system 1212 may be separate from or integrated with the processor 1206 of the computer 1204. The computer could also be configured with an input interface 1210 to receive input images from a user, or directly from the first or second imaging modalities; and an output interface 1210 such as a display to output the images taken, and the data collected to the user, or to directly send the ROI information to the second imaging modality. For example, these outputs may be the raw CAM or CNN data, heat maps, and the like. The system may also include memory 1208, such as RAM, ROM, flash memory, hard disks, and the like for storing the images and associated data. Of course, the first and second modalities may be the same (and comprised of common hardware features), for example, if the horizontal image and ROI image data are both (or come from) 3D OCT volume data sets collected from a single scan (as in the embodiment of FIG. 10). Similarly, depending on the embodiment, the processor 1206, memory 1208, computer 1204, and/or the like may be integrated with the imaging modalities (or lone modality) 1200, 1202, or wholly separate and simply supplied with imaging data to be analyzed. The elements of the computer 1204 may also be fully integrated into a single device, or separated as multiple devices, for example, if the machine learning system 1212 is embodied on a separate computer device.

Tests and Results

The above system and methods have been tested using public datasets (e.g., publically available retinal image sets from the Structured Analysis of the Retina (STARE) Project) to characterize the performance of different types of machine learning models and configurations (e.g., how many layers are trainable and how the ROIs are extracted). The tests were performed on a computer with a Core i7 CPU and Titan Xp GPU.

Table 1 below illustrates the specificity and sensitivity for various configurations of models and trainable convolution layers using roughly 400 fundus images having a resolution of 500×500 for training, with 39 possible retinopathy manifestations. Conv(X) in the table refers to a convolution layer with X number of filters.

TABLE 1

Example machine learning configurations

| Model | Configuration | # of trainable convolution layers | Specificity | Sensitivity |
|---|---|---|---|---|
| Xception | Add an additional Conv(20) to the end of the model | 1 | 87% | 30% |
| | Replace the final convolution layer with Conv(20) | 1 | 80% | 47% |
| | | 2 | 93% | 37% |
| Inception (V3) | Add an additional Conv(2048) layer to the end of the model | 1 | 81% | 34% |
| ResNet50 | Add an additional Conv(20) layer after the final activation layer | 1 | 88% | 47% |
| | | All layers | 83% | 48% |
| | Add an additional Conv(20) layer before the final activation layer | 1 | 91% | 44% |
| | | All layers | 92% | 14% |

TABLE 1-continued

Example machine learning configurations

| Model | Configuration | # of trainable convolution layers | Specificity | Sensitivity |
|---|---|---|---|---|
| InceptionResNetV2 | Add an additional Conv(20) to the end of the model | 1 | 87% | 63% |
| | | ~20% of all layers | 79% | 41% |
| MobileNet | Add an additional Conv(1024) to the end of the model | All layers | 83% | 31% |
| | Replace the final convolution layer with Conv(1024) | 1 | 62% | 68% |
| | | All layers | 81% | 34% |
| VGG16 | Add an additional Conv(512) to the end of the model | 1 | 93% | 91% |
| | | 4 | 86% | 98% |
| | | 7 | Does not converge | |
| | Replace the final convolution layer with Conv(512) | 1 | 92% | 97% |
| | | 3 | 84% | 100% |
| | | 6 | Does not converge | |
| VGG19* | Add an additional Conv(512) to the end of the model | 1 | 96% | 92% |
| | | 5 | 86% | 100% |
| | | 9 | Does not converge | |
| | Replace the final convolution layer with Conv(512)* | 1 | 86% | 100% |
| | | 4* | 88%* | 98%* |
| | | 8 | 82% | 100% |

As can be seen from the table, the training models achieved a good sensitivity and specificity. Thus, whereas previous machine learning studies trained and utilized one model for one type of disease, the systems and methods disclosed herein are capable of achieving high sensitivity and specificity while utilizing single models for identifying 39 different retinopathy manifestations. This success is possible with a variety of different models. While 39 retinopathy manifestations were tested, a more complex dataset (one with more retinopathy manifestations) could be used to provide the high sensitivity and specificity with more retinopathies. Thus there is no limit to the number of retinopathies to which the present disclosure can be applied. Of course the aspects of the present disclosure may be used with other models, machine learning algorithms, and methods of extracting information from those models, including those designed specifically for use with the present disclosure.

It is noted that example images shown in FIGS. 4-8 were formed from the VGG19 model, where the final convolution layer was replaced with Conv(512), with four trainable convolution layers. This configuration is identified with an asterisk in the above table.

What is claimed is:

1. An imaging method, comprising:

generating a horizontal image of an object;

automatically identifying a region of interest (ROI) of the object with a non-fully-supervised machine learning system, the non-fully-supervised machine learning system being trained to identify an abnormality of the object from the horizontal image;

generating a second image of the object within the identified ROI, wherein the second image comprises depth information of the object, wherein the method further comprises obtaining a class activation map from the non-fully-supervised machine learning system, wherein the non-fully-supervised machine learning system comprises a convolutional neural network (CNN), wherein each element of the class activation map corresponds to a weighted value of an activation map for a corresponding location of the horizontal image, the activation map being one of a plurality of activation maps produced by a final convolutional layer of the CNN, and wherein the ROI is identified based on the obtained class activation map.

2. The method of claim 1, wherein a global activation pooling (GAP) layer is attached to the final convolutional layer of the CNN, wherein the GAP layer comprises a plurality of values, each of the plurality of values corresponding to a different one of the plurality of activation maps, and wherein the weight applied to each activation map is determined during a training of the non-fully-supervised machine learning system, and relates a likelihood that the object has the abnormality to a value of the GAP layer at the corresponding location of the horizontal image.

3. The method of claim 1, further comprising:

normalizing or scaling values of the class activation map.

4. The method of claim 1, further comprising:

displaying the class activation map as a heat map superimposed on the horizontal image.

5. The method of claim 1, wherein the horizontal image is a color fundus image; an infrared fundus image; a scanning laser ophthalmoscope (SLO) image; or is derived from 3D optical coherence tomography (OCT) scan data.

6. The method of claim 1, wherein the second image is an OCT image.

7. The method of claim 1, wherein the horizontal image is derived from 3D optical coherence tomography (OCT) scan data, and the second image is an OCT image generated by extracting a portion of the 3D OCT scan data corresponding to the identified ROI.

8. The method of claim 1, wherein the horizontal image is derived from a 3D survey image and the second image has a greater density than the horizontal image.

9. The method of claim 1, wherein the abnormality is a retinopathy disorder.

10. A method of image analysis with a trained non-fully-supervised machine learning system, comprising:

receiving a horizontal image of an object from a subject;

identifying an abnormality of the object as an output of the trained non-fully-supervised machine learning system based on the received horizontal image;

extracting information of the trained non-fully-supervised machine learning used to identify the abnormality;

identifying a region of interest (ROI) within the horizontal image as a region of the horizontal image that contributed to the identification of the abnormality, wherein the non-fully-supervised machine learning system is trained with a plurality of horizontal images of the object from different subjects to identify the abnormality of the object, wherein the information of the trained non-fully-supervised machine learning system is extracted by obtaining class activation maps, wherein the non-fully-supervised machine learning system comprises a convolutional neural network (CNN), wherein each element of the class activation map corresponds to a weighted value of an activation map for a corresponding location of the horizontal image, the activation map being one of a plurality of activation maps produced by a final convolutional layer of the CNN, and wherein the ROI is identified based on the obtained class activation map.

11. The method of claim 10, wherein a global activation pooling (GAP) layer is attached to the final convolutional layer of the CNN, wherein the GAP layer comprises a plurality of values, each of the plurality of values corresponding to a different one of the plurality of activation maps, and wherein the weight applied to each activation map is determined during a training of the non-fully-supervised machine learning system, and relates a likelihood that the object has the abnormality to a value of the GAP layer at the corresponding location of the horizontal image.

12. The method of claim 10, further comprising: normalizing or scaling values of the class activation map.

13. The method of claim 10, further comprising: displaying the class activation map as a heat map superimposed on the horizontal image.

14. The method of claim 10, wherein the horizontal image is a color fundus image; an infrared fundus image; a scanning laser ophthalmoscope (SLO) image; or is derived from 3D optical coherence tomography (OCT) scan data.

15. The method of claim 10, wherein the abnormality is a retinopathy disorder.

* * * * *